(12) United States Patent
Fu et al.

(10) Patent No.: US 9,114,094 B2
(45) Date of Patent: Aug. 25, 2015

(54) METHOD OF USE AND PREPARATION OF HSA FUSION PROTEIN COMPOSITION FOR SKINCARE

(71) Applicants: Yan Fu, New York, NY (US); Zailin Yu, New York, NY (US)

(72) Inventors: Yan Fu, New York, NY (US); Zailin Yu, New York, NY (US)

(73) Assignee: TIANJIN SINOBIOTECH LTD., Tianjin (CN)

(*) Notice: Subject to any disclaimer, the term of this patent is extended or adjusted under 35 U.S.C. 154(b) by 0 days.

(21) Appl. No.: 14/064,701

(22) Filed: Oct. 28, 2013

(65) Prior Publication Data
US 2014/0099270 A1   Apr. 10, 2014

Related U.S. Application Data

(62) Division of application No. 12/529,981, filed as application No. PCT/CN2008/072485 on Sep. 24, 2008, now Pat. No. 8,603,973.

(30) Foreign Application Priority Data

Sep. 25, 2007   (CN) .......................... 2007 1 0059770

(51) Int. Cl.

| | | |
|---|---|---|
| *A61K 38/00* | (2006.01) |
| *A61K 38/16* | (2006.01) |
| *A61K 38/17* | (2006.01) |
| *A61K 38/18* | (2006.01) |
| *C12N 15/00* | (2006.01) |
| *C12N 15/09* | (2006.01) |
| *C12N 15/11* | (2006.01) |
| *C12N 15/12* | (2006.01) |
| *C12N 15/62* | (2006.01) |
| *C12N 15/63* | (2006.01) |
| *C12N 15/81* | (2006.01) |
| *A61K 8/64* | (2006.01) |
| *A61K 9/00* | (2006.01) |
| *A61K 9/06* | (2006.01) |
| *A61K 9/107* | (2006.01) |
| *A61K 38/38* | (2006.01) |
| *A61Q 19/02* | (2006.01) |
| *A61Q 19/08* | (2006.01) |
| *C07K 14/475* | (2006.01) |
| *A61K 38/19* | (2006.01) |
| *A61K 38/20* | (2006.01) |
| *A61K 38/21* | (2006.01) |
| *A61K 38/30* | (2006.01) |
| *A61K 36/064* | (2006.01) |
| *A61K 8/99* | (2006.01) |
| *A61Q 5/12* | (2006.01) |
| *A61Q 11/00* | (2006.01) |
| *A61Q 19/00* | (2006.01) |

(52) U.S. Cl.
CPC ... *A61K 8/64* (2013.01); *A61K 8/99* (2013.01); *A61K 9/0014* (2013.01); *A61K 9/06* (2013.01); *A61K 9/107* (2013.01); *A61K 36/064* (2013.01); *A61K 38/1808* (2013.01); *A61K 38/1816* (2013.01); *A61K 38/1858* (2013.01); *A61K 38/193* (2013.01); *A61K 38/20* (2013.01); *A61K 38/217* (2013.01); *A61K 38/30* (2013.01); *A61K 38/38* (2013.01); *A61Q 5/12* (2013.01); *A61Q 11/00* (2013.01); *A61Q 19/00* (2013.01); *A61Q 19/02* (2013.01); *A61Q 19/08* (2013.01); *C07K 14/475* (2013.01); *C07K 2319/00* (2013.01)

(58) Field of Classification Search
None
See application file for complete search history.

(56) References Cited

U.S. PATENT DOCUMENTS 8,603,973 B2 * 12/2013 Fu et al. ................. 514/9.6
2006/0195945 A1 *  8/2006 Lee et al. ................ 800/288

OTHER PUBLICATIONS

Barrientos et al. (2008, Wound Rep. Reg. 16:585-601).*

* cited by examiner

*Primary Examiner* — Elizabeth C Kemmerer
(74) *Attorney, Agent, or Firm* — CUSPA Technology Law Associates, P.A.; Yi Li

(57) ABSTRACT

The present invention provides a recombinant fusion protein which stimulates the rejuvenation and reactivation of skin and epidermal cells for improving skin appearance, smoothing wrinkles and freckles, and whitening skin. Particularly, the present invention provides various types of products for improving skin, which contain recombinant fusion protein of human serum albumin (HSA) with cytokine peptides (EGF, FGF, KGF, HGH, HGF, PDGF, GCSF, interferon, IL-11 or IGF) by genetic engineering technology. The fusion protein can be used independently or in a combination or combination with yeast fermentation products, or with varied emulsifiers, thickeners, moisturizer, preservatives, yeasts and ferments.

15 Claims, 5 Drawing Sheets

The results of total protein, total polysaccharide and A350/280 ratio from fermentation media processed by different concentrations of charcoal (Fig. 3-A partial)

| No. | Charcoal (%) | Total Polysaccharide (μg/ml) | Total Protein (μg/ml) | Density ratio (A350/280) |
|---|---|---|---|---|
| 1 | 0 | 1104.310 | 5.40 | 1.005 |
| 2 | 2 | 413.362 | 1.95 | 0.067 |
| 3 | 5 | 318.534 | 1.66 | 0.070 |
| 4 | 7 | 259.914 | 1.22 | 0.060 |
| 5 | 10 | 159.259 | 1.01 | 0.071 |

METHOD OF USE AND PREPARATION OF HSA FUSION PROTEIN COMPOSITION FOR SKINCARE

RELATED APPLICATIONS

This application is a divisional of U.S. application Ser. No. 12/529,981, filed Oct. 20, 2010, now issued as U.S. Pat. No. 8,603,973 B2, which is a national phase of PCT Application No. PCT/CN2008/072485, filed Sep. 24, 2008, which claims priority of Chinese Patent Application No. 200710059770.3, filed Sep. 25, 2007. The parent applications are incorporated by reference.

The present invention is a continuation of Chinese Patents ZL021428816, ZL2004100428148 and Chinese Patent Application 200710057571.9. The present invention involves methods for the combination and preparation of recombinant human serum albumin fusion proteins for novel gene-related skincare; wherein a single fusion protein or combinations of different proportion of fusion proteins or combination of fusion protein and yeast fermentation products, Polysaccharide and yeast protein). The present invention particularly focuses on combinations of fusion protein (HSA/GF) of human serum albumin (HSA) and human growth factor (GF) in making novel skincare products. The growth factors include, but are not limited, human epidermal cells growth factor (EGF), fibroblast growth factor (FGF), platelet-derived growth factor (PDGF), keratinocyte growth factor (KGF), insulin-like growth factor (IGF), TGF, GCSF, interferon and IL-11 etc. The combinations can also include moisturizers, thickeners, emulsifiers, preservatives, yeasts and fermentation products and/or extracts from animals and plants etc. The skincare products of present invention have unexpected advantages and good effectiveness when in use.

BACKGROUND TECHNOLOGY

Skincare compositions, sometimes including cosmetics, are daily necessities in modern human life. All types of skincare compositions including moisturizers, wrinkle removers, freckle removers, whitening, and acne treatments are used to improve quality of life and solve the problems of aged skin due to damage, degeneration and decreased skin function, etc. Various chemicals, extracts from animals and plants, tissue extracts of human origin and polypeptides of recombinant protein have been used as additives and active ingredients to make skincare compositions. Among these are, human epidermal cell growth factor (EGF), fibroblast growth factor (FGF) and human serum albumin (HSA) from human origin or recombinant gene expression product. As cytokines are amino acids and peptides, their shelf life and half-life in plasma and in exposing on skin surface are short. Therefore, it is necessary to add protective agents to prolong their shelf life and effective half-life in vivo. In the Chinese Patent Application 200710057571.9 of Yu, Zailin, it is shown that protein fusion technology of fusing the human skin cell growth factors with HSA and validates prolongs the half-life of these cytokines.

Human serum albumin is a soluble, monomeric protein which comprises about one-half of the blood serum protein. Albumin functions primarily as a carrier protein for steroids, fatty acids, and thyroid hormones and plays a role in stabilizing extracellular fluid volume. Albumin is a globular non-glycosylated serum protein of molecular weight 65,000 with 585 amino acids. Proalbumin, is cleaved in the Golgi vesicles to produce the secreted albumin. HSA has 35 cysteines; in blood this protein monomer has 17 disulfide linkages (Brown, J. R. "Albumin structure, Function, and Uses" Pergamon, N.Y., 1977). At present, albumin for clinical use is produced by extraction from human blood. The production of recombinant albumin (rHSA) in microorganisms has been disclosed in EP 330 451 and EP 361 991, and in China patent ZL2004010057313.7 of Yu, Zailin. Albumin is the most abundant plasma protein in human blood with 40 g per liter, and with a high plasma half-life 14-20 days.

When growth factors are fused with albumin, to form compounds according to this invention the fusion protein has the advantage of resisting enzymatic degradation in vivo and prolonged sustainable half-life in vivo and shelf life in vitro. Also after fusion, it allows use of a high dosage of fused cytokine, and use of the fusion protein produces less toxicity than occurs when the cytokine is used alone.

Albumin from human blood or recombinant human serum albumin has been used in skincare. For example, human serum albumin was used as an ingredient in the anti-wrinkle product disclosed in EP 0180968A3, and used in skin cleaners and shampoos are disclosed in PCT application WO02/49671A1. It was described in detail in U.S. patent application Ser. No. 10/446,562 that combination of human serum albumin and *Bacillus botulinus* was used as therapeutic skincare. PCT application WO01/91713A1 describes the use of human serum albumin from transgenic animal in skincare compositions. U.S. Pat. No. 5,948,609 disclosed the whole length or fragment or modified albumin in skincare compositions. Chinese Patent applications CN02111695, CN1090753, CN93105601.2 and CN01810411.8 describe human albumin used as an additive and a protective agent in skincare. Chinese Patent application CN200610081498.4 focused on describing formulation and procedure in production of recombinant albumin and yeast ferment for moisturizing skin, smoothing wrinkles and whitening skin.

Albumin is also often used as stabilizer in pharmaceutical formulation, especially in biologicals.

With gene recombinant engineering technology, a fusion protein can be expressed in yeast linking a therapeutic protein gene product and human serum albumin having improved stability and half life for the therapeutic protein in plasma and storage stability to achieve a long-lasting effect. The technology platform for the making of such fusion proteins (such as the modified protein drug of this invention (in vivo is cited as a reference here), which has been disclosed in Chinese Patents ZL02142881.6 and ZL200410042814.8 by Yu, Zailin and Fu, Yan). The human serum albumin fusion protein of this invention is used in making skincare compositions with improved cytokines's half-life and has an optimal clinical effect in the application of novel gene skincare products.

Procedures for formulating and producing skincare compositions comprising these fusion proteins are the same as the known methods of skincare composition production described in the literature of the field. The book "Cosmetics-principals, formulation and production procedure" is a main reference, written by Wang Peiyi, 2nd edition 2006, published by Chemistry Industry Press.

SUMMARY OF THE INVENTION

The present invention involves the formulation and production procedure of skincare compositions comprising fusion protein of human serum albumin and epidermal cell growth factor, and involves particular areas:

1) A skincare composition comprising fusion protein or its functional fragment, wherein the fusion protein is fused from human serum albumin (HSA) and a skin cell growth factor (GF).

2) A skincare composition comprising a fusion protein 1) wherein the fusion protein comprises one or several of following: human serum albumin (HSA)/insulin-like growth factor (IGF), HSA/fibroblast growth factor (FGF), HSA/epidermal cell growth factor (EGF), HSA/platelet-Derived Growth Factor (PDGF) and HSA/keratinocyte growth factor (KGF), HSA/endothelial cell growth factor (VEGF).

3) A skincare composition described above 1) or 2), wherein the fusion protein is the composition of HSA/hEGF and HSA/KGF or the combination of HSA/IGF and HSA/PDGF.

4) A skincare composition described above 1)-3) also comprises one or several of following: HSA, HSA/Granulocyte colony-stimulating factor (GCSF), HSA/interferon (IFN) or/and HSA/interleukin.

5) A skincare composition described above 1)-4), wherein the composition comprises one or several of following ingredients: excipients, water retention agents, preservatives, whitening agents, thickeners or/and emulsifiers.

6) A skincare composition described above 1)-5) wherein the composition comprises one or several of following drugs: antibiotics, anti-virus drugs and anti-infection drugs.

7) A skincare composition described above 1)-6) wherein the composition is in one of following forms: aqueous solution, ointment, suppository, cream, and face membrane.

8) A skincare composition described above 1)-7) wherein the fusion protein is purified by column chromatography.

9) A skincare composition described above 1)-7) wherein the fusion protein is processed by incubating at appropriate conditions, host cells which express the described fusion protein centrifuging culture media, de-coloring, de-salting and concentrating the supernatant.

10) A skincare composition described above 9) wherein the host cells are cells from bacteria, fungal, plants and animals; wherein the fungal are from yeast; and wherein the yeasts are *Saccharomyces*, *Pichia*, *Kluyveromyces*, *Candida*, *Hancenula*, *Tarulaspora* and *Schizosaromyces*. Preferably, the host system is *Pichia pastoris*, the most preferred one of yeast expression strains is CGMCC 2072 (patent deposit at China General Microbiological Culture Collection (CGMCC) center).

11) A skincare composition described above 10) wherein the yeast culture medium contains yeast polysaccharide and yeast protein, and the fusion protein of human serum albumin and cell growth factor and its fragments is produced by fermentation.

12) A skincare composition described above 1)-11) wherein it is used to promote skin beauty, moisture retention, wrinkle removal, wrinkle prevention, skin whitening and epidermal cell rejuvenescence and reactivation, acne removal, anti-infection; and treating wounds, burns and disease.

13) A skincare composition described above 1)-11) wherein the production procedure includes:
  i) culturing the host cell to express fusion protein at appropriate culture conditions;
  ii) purifying the fusion protein from i) by column chromatography;
  iii) adding the product from ii) to the described combination.

14) A skincare composition described above 1)-11) wherein production procedure includes:
  i) culturing the host cell to express fusion protein at appropriate culture conditions;
  ii) centrifuging, de-coloring, de-salting and concentrating media obtained from i);
  iii) adding the product from ii) to the described combination.

15) A procedure described above 14) can include mixing fermentation media which express two or more types of fusion proteins before procedure ii).

16) The procedures described above 13) or 14) ii) can include adding excipients to the product obtained the product.

17) The procedures described above 14) or 15) ii) can include adding excipients to the product obtain lyophilizing product.

18) The procedures described above 13)-14) ii) can include the de-coloring by use of 0.1%-10% (w/w) active charcoal or diatomite.

19) A product described above 1)-11) is used for skin care use.

20) A product described above 1)-11) can include one or several following materials: cotton, non-woven fabrics, gauze, wood pulp, bio-fibre for skin care use.

21) A product described above (20) can be a face membrane, neck membrane, nose membrane, eye membrane or/and body membrane.

The embodiments of the present invention comprising fusion proteins of human serum albumin and human skin cell growth factor (GF) have been shown to have better effect than compositions comprising only GF monomer or only albumin. Cytokines fused with albumin have extended half-life, and subsequently possess sustainable effect in vivo and in vitro. It has a multiple synergistic ability to activate skin cells when fusion proteins of HSA and various growth factors (HSA/GF) are in combinations. The novel skincare can be used in cosmetics, anti-wrinkle, anti-freckle, and whitening products and can also be used to treat ulcerations, wounds and burns, including those associated with cosmetic surgery.

BRIEF DESCRIPTION OF THE FIGURES

FIG. 3A) HSA/GCSF fusion protein in 30 L fermentation media processed by 0% 0.4%, 1%, 2%, 5%, 7%, 10% amount of charcoal; FIG. 3B) total protein from fermentation media processed by 0%, 0.4%, 1%, 2%, 5%, 7%, 10% diatomite. Different cytokines, cell stimulating factors or polypeptides, fused with human serum albumin have very similar de-coloring result by charcoal or by diatomite.

FIG. 4 The table shows of the results of total protein, total polysaccharide and A350/280 ratio from fermentation media processed by different concentrations of charcoal.

FIG. 6A) preparation 1-solution; FIG. 6B) preparation 2-water gel; FIG. 6C) preparation 3-emulsifier; FIG. 6D) preparation-4 cream, ointment; FIG. 6E) preparation 5-colored acne treatment cream (containing antibiotics SULFASALAZINE); FIG. 6F) Facial membrane containing preparation 1.

DETAILED DESCRIPTION OF THE INVENTION

Figure 1:
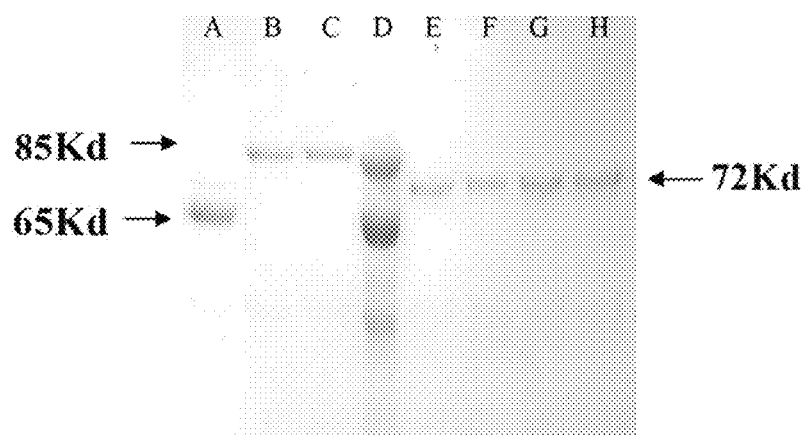
FIG. 1 shows the purity of different fusion proteins expressed in yeast.
A) HSA; B) HSA/KGF-2; C) HSA/bFGF; D) Standard MW; E) HSA/hEGF; F) HSA/hEGF; G) HSA/hIGF; H) HSA/hIGF.

The present invention involves the use of a fusion protein of human serum albumin and skin cell growth factor (GF) which include, but are not limited, human serum albumin and human epidermal cells growth factor (EGF), fibroblast growth factor (FGF: aFGF, bFGF), platelet-derived growth factor (PDGF), keratinocyte growth factor (KGF-2), insulin-like growth factor (IGF), or interleukin (IL-11), or granulocyte colony stimulating factor (GCSF). The fusion protein can be used in making skincare compositions having full length, modified or fragments of growth factors or the albumin.

The fusion protein can be used independently or combined with albumin or other albumin fusion proteins, and can be further used with one or several excipients, thickeners, emulsifiers, moisturizer to make skincare products for skin cell reactivation, plastic surgery recovery, burn treatment or other uses.

The albumin fusion proteins can be used in various skincare preparations, including, but not limited to, various solutions such as freshness toning waters, conditioners, toner, shampoo, conditioner, deodorant liquids, gargles; various creams such as face cream, eye cream, hand cream, body lotion, sunscreen cream, cold cream, shampoo, tooth pastes, anti-wrinkle creams; various emulsions such as water-in-oil emulsions, oil-in-water emulsions; suppositories such as vaginal suppositories, anal suppositories; membranes such as shaped membrane (cotton membrane, paper membrane, non-woven fabrics, collagen); paste membrane etc. The skincare compositions containing the fusion protein described in the present invention can also comprise other specially functional ingredients, including but not limited to, milk, pearl powder, honey, herbal medicine, plant extracts (e.g. aloe, ginseng), animal extracts (e.g. snail, placenta). It can also be combined with antibiotics for acne treatment products. The fusion protein in present invention can be used to make specially functional skincare products which include, but are not limited to, face cleaners, exfoliating scrubs, nutrition, massage, acne treatments, freckle treatments, cleansers for nose skin, and beauty products.

The fusion protein in the novel skincare product can be made with 95% purity by purifying from the supernatant of large-scale yeast fermentation, and also can be produced simply by de-coloring and de-salting and concentrating the supernatant of yeast fermentation to keep fusion protein and yeast secretion (polysaccharide and yeast proteins) to make novel skincare products. Therefore, this invention involves the following areas:

1) Technology Solution for Using HSA/GF Fusion Protein in Skincare

The present invention provides a formulation and production procedure for the fusion protein of human serum albumin (HSA) and cell growth factor (GF) by using genetic engineering. The fusion proteins possess the properties of growth factors, including stimulating skin cell differentiation, proliferation and repair. The fusion protein described in the present invention can be an additive or the main ingredient in making a skincare product for whitening skin, removing freckle and wrinkles, among other things. Among the growth factors, skin cell growth factor (GF) is available in clinical use as a therapeutic for external use. For example, hEGF and hKGF have been approved for clinical use to treat burns and ulcerations, and the fusion protein properties of this invention can also be used for these purposes.

Any type of albumin or its variant can be fused with one type of GF to form albumin fusion protein. The GF in the present invention can be any one of following, but is not limited, epidermal cells growth factor (EGF), hepatocyte growth factor (HGF), nerve cell growth factor (NGF), fibroblast growth factor (FGF), endothelial cell growth factor (VEGF), insulin-like growth factor (IGFL), stem cell growth factor (SGF), stem cell factor (SCF), keratinocyte growth factor (KGF), Platelet-Derived Growth Factor (PDGF), and growth hormone released factor (GHRF or GHRH) etc.

The GF can be linked directly to the N-terminus or the C-terminus of HSA to form an HSA-GF fusion. Optionally, there is a peptide linker (L) linking HSA and GF together to form the fusion protein: HSA/L/GF or GF/L/HSA (L=linker). The length of the peptide linker is preferably between 2-100 amino acids, more preferably between 10-50 amino acids, and most preferably between 14-30 amino acids. The peptide linker can be a flexible linker that minimizes steric hindrance imposed by the bulky HSA protein on GF, such as a $(G.sub.4S).sub.3-4$ linker. The linker in the fusion protein can have immunogenicity, so preferably, there is no linker in between of the fusion protein.

The fusion protein is a secretory protein, which binds to a specific antibody of human albumin, and optionally, binds to a specific antibody of the GF of the fusion protein. Secretion signal peptide of fusion protein can be the albumin secretion signal peptide or naturally existed polypeptide or artificially synthesized polypeptide that secret fusion protein out of host cell.

In one embodiment, the inventors of the present invention obtained the nucleotide sequences encoding HSA/hKGF-2, HSA/hEGF, HSA/hIGF1, HSA/hbFGF, HSA/haFGF and HSA/hPDGFB; and their corresponding amino acid sequences encoding proteins/polypeptides by genetic engineering. Up to 5% of the stated nucleotide sequences can be substituted, deleted, inserted or added, as described in Chinese patent application CN200710057571.9.

HSA/GF nucleotide sequences of the present invention can be introduced to host cell by gene cloning techniques to express the fusion protein. Generally, host cells are genetically engineered (transducted or transformed or transfected) with the vectors of the present invention which can carry any or all possible combinations of HSA/GF. The vector can be, for example, in the form of a plasmid which invades to host system, a viral particle as a vector or shuttle bus which enters a host system. The engineered host cells can be cultured in conventional nutrient media modified as appropriate for activating promoters, selecting transformants or amplifying the polynucleotides encoding HSA/GF fusion proteins. The culture conditions, such as temperature, pH and the like, are those conventionally used with the host cell selected for expression.

Expression in the host cell of the polynucleotide encoding an HSA/GF fusion protein is under the control of a suitable promoter. Suitable promoters which can be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, heat shock promoters; the albumin promoter; the ApoAI promoter; human globin promoters; viral thymidine kinase promoters, such as the Herpes Simplex thymidine kinase promoter; retroviral long terminal repeats (LTR's) including the modified retroviral LTRs; the β-actin promoter; and human growth hormone promoters. The promoter also can be the native promoter which controls the polynucleotide encoding an HSA/GF fusion protein.

According to the invention, a recombinant vector is provided that comprises the polynucleotide sequence encoding an HSA/GF fusion protein. The recombinant vectors can be an expression vector for expressing the fusion protein encoded by the nucleic acid in a host organism. The expressed fusion proteins can be, but are not limited HSA/CPSA, GF/HSA, HSA/L/GF or GF/L/HSA (where L=linker). The host organism includes, but is not limited to, vertebrates (e.g., human, monkey, mouse, rabbit, etc.), fish, chickens, insects, plants, yeast, fungi, bacteria etc.

Also according to the invention, a recombinant cell is provided that is capable of expressing the polynucleotide sequence encoding an HSA/GF fusion protein. The recombinant cell can be induced in the presence or absence of an agent to express the fusion protein encoded by the nucleic acid, HSA/GF, HSA/L/GF, or GF/L/HSA in a host organism. The type of the recombinant cell includes, but is not limited to, vertebrate (e.g., human, cattle, swine, monkey, mouse, rabbit, fish, chicken etc.), insects, plants, yeast, fungi, and bacterial cells.

Depending upon the host employed in the recombinant process for producing the fusion proteins, the fusion proteins of the present invention can be glycosylated or can be non-glycosylated. Preferably, when expressed in a host organism, the fusion protein of HSA and GF can be glycosylated to substantially the same extent as that when expressed in mammalian cells such as by the use of Chinese hamster ovary (CHO) cells, whereas the fusion protein is non-glycosylated or semi-glycosylated when expressed in *Pichia* yeast.

As a specific embodiment of HSA/GF fusion protein in the use of novel skincare, the recombinant yeast expressing fusion protein HSA/hEGF has been deposited at China General Microbiological Culture Collection (CGMCC) Center, No. CGMCC No. 2072. This is a representative embodiment for the usage of HSA/GF from the present invention in novel skincare product.

As indicated above, the albumin fusion proteins of the present invention are substantially preferably generated by the techniques of genetic engineering. The preferred way to obtain these fusion proteins is by the culture of cells transformed, or infected by vectors expressing the fusion protein. In particular, expression vectors are capable of transforming yeasts, especially the genus *Pichia*, which secrete fusion proteins in the growth media.

2) Procedure for Large-Scale Production of HSA/GF Fusion Protein Expression

The fusion protein HSA/GF of present invention is expressed in yeast host cells by recombinant DNA techniques. The yeast host for expressing fusion proteins can be, but is not limited to, *Saccharomyces, Pichia, Kluyveromyces, Candida, Hancenula, Tarulaspora* and *Schizosaromyces*. Preferably, the host system is *Pichia pastoris*.

In summary, it is particularly advantageous to express the HSA/GF fusion protein in yeast. Such an expression system allows for production of high quantities of the fusion protein in a mature form, which is secreted into the culture medium, thus facilitating purification. Yeast secretion in growth media is composed of a large amount of yeast polysaccharide and yeast proteins. The fusion protein and yeast secretion can be isolated by generally known techniques and then further used as ingredients or additives for skincare product production.

In a preferred embodiment, a particular species of yeast, *Pichia pastoris*, is used as the system for expressing HSA/GF fusion proteins of the present invention. *Pichia* has many of the advantages of higher eukaryotic expression systems such as protein processing, protein folding, and post-translational modification, as well as easy large-scale production as seen with cultures of bacteria and *Saccharomyces cerevisiae*. It is faster and easier to use than other eukaryotic expression systems such as mammalian tissue culture, and generally gives higher expression levels. *Pichia* has an additional advantage which gives 10 to 100-fold higher heterologous protein expression levels. These features make *Pichia* very useful as a protein expression system.

Yeast fermentation procedure which produces fusion protein in skincare is described in China Patent ZL200410057313.7 by Yu, Zailin. The fusion proteins secreted to fermentation media by inducing yeast at 30° C. for 20° C., preferably at 20° C.

The fusion protein expressed by yeast which is described in the present invention can be purified by any of the conventional methods that keep the fusion protein's bio-activity and cytokine's bio-function. After the fermentation, the cell culture media are centrifuged to separate the yeast cell and the supernatant. The fusion protein and its fragment (degraded protein), yeast proteins and polysaccharide can be isolated from the supernatant. The supernatant is de-colored by adding 0.4-10% (W/V) activated charcoal or diatomite, preferably 2% activated charcoal. Upon further de-salting by conventional means, such as SEPHADEX G-25 MEDIUM, the fermentation media (supernatant) becomes a colorless and tasteless albumin-like liquid which is further concentrated by 10-20 times through 20K dialysis membrane. The concentrated samples can be used as main ingredient for producing skincare products or as aliquots to small packages or then making as a lyophilized form for making skincare products.

It is noted that other expression systems can also be used to express HSA/GF fusion proteins in the present invention, including but not limited to, *B. subtitis, Saccharomyces, Kluyveromyces, Hansenula, Candida, Torulopsis, Torulaspora, Schizosaccharomyces, Citeromyces, Pachysolen, Debaromyces, Metschunikowia, Rhodosporidium, Leucosporidium, Botryoascus, Sporidiobolus, Endomycopsis*, animals, plants, and insect cells.

3) HSA/GF Fusion Protein Combination Used for Making Skincare

After entering into the body, the HSA/GF fusion protein has the plasma half life at least 2 times longer than that of the GF monomer itself, preferably 4 times, further preferably 6 times and most preferably 10 times longer half-life. The HSA/GF fusion protein of the present invention can be used in combination with naturally isolated or recombinant human serum albumin, preferably with recombinant human serum albumin at effective dosages and ratios.

Cytokines acquire extended half-life and sustained long acting time in vivo after they form the HSA/GF fusion protein, which reduces dosage and frequency of daily use. Therefore, the shelf life is longer and shipping requirements are less, and subsequently reduces costs.

The present invention can be used in functional skincare products containing fusion protein. For instance, skin care, moisture retention, anti-wrinkle, wrinkle smoothing, and skin whitening products. The formulation can compose of one type of fusion protein or two or more types of fusion proteins, or other ingredients like HSA as a main ingredient, or other thickeners, emulsifiers, moisturizer, preservative.

Therefore, the present invention provides combinations of different fusion proteins for use of making skincare preparations.

The distinctive combinations of fusion proteins can be administered to a patient to stimulate proliferation of multiple types of skin cells or to synergistically enhance proliferation of a particular cell type. In particular, combination use of the fusion proteins of HSA and the use of different active cytokines can promote the proliferation and maturation of multiple cells simultaneously. Due to the characteristics of HSA/GF targeting the signal transduction pathways of different types of cells or multiple functional cell production, epidermis cell, keratinocyte and muscle cell, fibroblast can be proliferated and remedied once administration.

The present invention provides description and embodiments of different combinations of HSA/GF in making skincare products, which include a first HSA/GF and a second HSA/GF which can be a different product from the first HSA/GF. For example, the first GF in the HSA/GF is KGF and the second GF is EGF; or the first GF is GKF-2 and the second GF is bFGF, the third GF is EGF; or the first GF is IGF-1 and the second GF is FGF. HSA monomer can be the first or second protein ingredient in combination formulation. Albumin fusion protein described in the present invention can be used as single ingredient in skincare. The fusion protein can be purified to 95% purity or higher, or the fermentation product containing fusion protein can be de-colored, de-salt and de-taste and concentrated for use as a main ingredient of various skincare products. The combined yeast media of two or more than two fusion proteins (such as HSA/hEGF and HSA/bFGF, or HSA/hEGF, HSA/bFGF and HSA/hKGF-2), or combined fusion proteins can have better effect for making skincare products.

The formulation of serum albumin fusion protein and known ingredients of skincare products in accordance with the present invention can be used in making various preparations of skincare products according to the invention, include but not are limited to, solutions, cream emulsions, ointments, suppositories or membranes, etc. The purified fusion monomer or processed yeast fermentation media including fusion proteins can be formulated with a moisture retention agent, emulsifiers, thickeners and preservatives or membrane materials with the ratio known among artisans in this technology area. The materials added in making skincare should have little effect on stability of fusion protein. The moisture retention agents are, but are not limited, various ethanols, propanediol, butanediol, propanetriol (glycerol), Vitamins C, A, E), fatty acids, cholesterol, hyaluronic acid, ceramide etc. Emulsifiers are, but are not limited to, tween or Span (20, 40, 60, 70, or 80), SDS, SLS, lecithin, cholesterin, etc. Thickeners are, but are not limited to, various esters, fats, oils, waxes, lanolin, fatty alcohols, Vaseline, mineral oil, carbomer, poloxamer etc. Preservatives are, but are not limited to, methyl-p-hydroxy benzoate, ethyl p-hydroxybenzoate, butylparaben, merthiolate etc. Membrane materials are, but are not limited to, cotton, non-woven fabrics, gauze, wood pulp, bio-fibre etc. The combination of fusion proteins and antibiotics can be used for treating acne, and its lesions (pimples), using both solution and cream formats.

All types of containers can be used to store the fusion protein products. The container must meet appropriate standards.

It is also known that "naked" cytokines are quite unstable when stored and have a short plasma half-life. Clearly, a therapeutic protein with such a weak stability in vivo constitutes a major handicap to its use. In effect, repeated injections of the product, which are costly and inconvenient for patients, become necessary to attain an effective concentration in plasma. In fact, albumin, as a kind of additive, is used with cytokines for prolonging shelf life to assure the stability during storage and shipping. The combination of human albumin and hEGF (not a fusion protein) for making skincare which has been described in China Patent Application CN200610081498.4, made the hEGF to acquire only extended shelf life. However, an embodiment using gene fusion technology in accordance of the present invention proved fusion protein have extended in vitro activity greater than EGF monomer or combination of EGF and HSA, at least three times longer than that of combination of cytokines and HSA and ten times longer than that of cytokines which is used alone, under the same conditions.

The fusion protein HSA/GF used in skincare, in accordance of present patent, has extended half-life and stability. Fused HSA/GFs, such as HSA with hEGF, HSA with hKGF, HSA with hIGF or HSA with hPDGF used alone or in a combination can stimulate therapeutic actions and proliferate of multi epidermal cells at same time.

In one embodiment, skincare combination containing HSA/hEGF fusion protein and HSA/hKGF fusion protein stimulates differentiation and proliferation of epidermal cells and keratinocytes. As a result, the recovery of the skin is faster.

Alternatively, one type of HSA/GF skincare product and another type of HSA/GF skincare product can be used simultaneously or sequentially. Combining dosage can reach the dosage of improving beauty effect obviously, which is the synergy dosage.

Furthermore, human serum albumin (HSA) or its fragments or modified HSA can be combined with albumin fusion protein as ingredients for making skincare products. Compared with use of albumin or cytokines independently, fusion protein or combined with different fusion proteins or metabolic products from yeast ferment has more advantages of extending cytokines' action, and subsequently enhance skin beauty.

EMBODIMENTS

Embodiment 1

Recombinant Yeast Fermentation Technology for Production of HSA/GF Fusion Proteins Several colonies of yeast expressing genes of human albumin, or fusion protein of albumin with KGF, albumin with bFGF, or albumin with hEGF (the yeast construct expression rHSA/EGF has been patent deposited at China General Microbiological Culture Collection (CGMCC) Center, Deposit Number CGMCC No. 2072, or albumin with hIGF, are cultured in the basic media including antibiotic Zeocin, buffer and glycerol. The media are incubated at 300 rpm in a thermostatic shaker until reaching a density of OD600=2-6. Cells are collected by centrifuging at 1500 rpm for 15 minutes and then suspended in similar media containing 0.5% methanol instead of glycerol until reaching cell density OD600=1.0. The foreign genes in the yeast are initiated by a promoter to start expression under the induction of methanol. Thereafter, to the media are added 100% methanol per 24 hours to final concentration of 0.5%, and then supernatant was collected after 48 hours. FIG. 1 shows 7.5% SDS-PAGE electrophoresis result of 20 µl fermentation media. The result indicates 70-80% of fermentation media are the desired protein with molecular weight similar to anticipated one.

Figure 2:
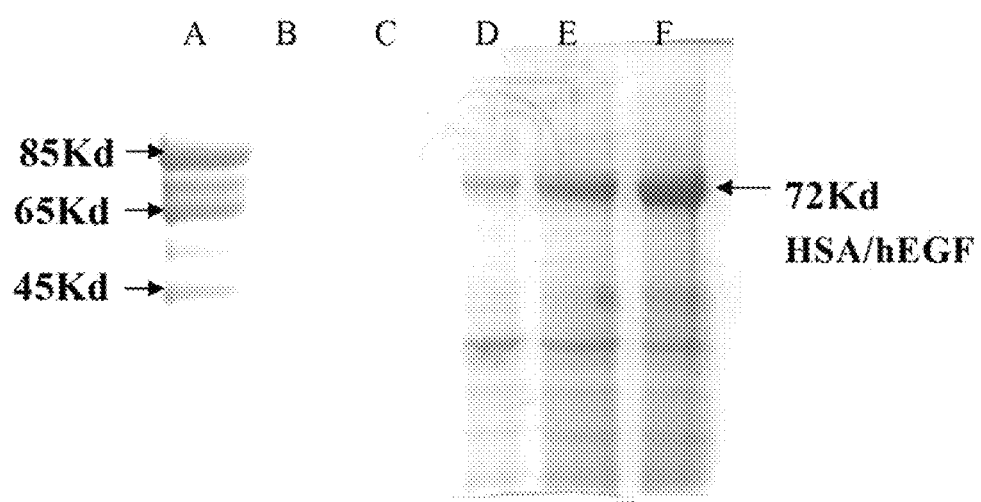
FIG. 2 shows the results of electrophoresis of fusion protein amount expressed at different inducing time points in a 30 L fermentor/bioreactor. The typical yeast strains expressed fusion protein of human serum albumin and cell growth factor is HSA/hEGF (has been Patent deposited at China General Microbiological Culture Collection (CGMCC) center: Deposit Number CGMCC No. 2072). The expression level of fusion protein expressed at different phase with inorganic salt in 30 L at a high density fermentation. 20 µl of supernatant from centrifuged fermentation media at different phase is analyzed by 10% SDS-PAGE gel. A) Standard MW; B) yeast cell in growth phase; C) in glycerol fed-batch phase; D) at methanol induced 24 hrs; E) at methanol induced 48 hrs; F) at methanol induced 72 hr. Result indicates: expression amount of fusion protein (HSA/hEGF) is 0.5-1.2 g/L at 72 hr methanol induction.

The strain validated in shaker test as having expressed the desired genes was cultured in large-scale 5 L or 30 L fermentator with inorganic media, which has been described in China Patent ZL200410057313.7 of Yu, Zailin. The strain was cultured at 30° C., or at 20° C. induced by methanol; preferably, at 20° C. to express fusion protein. The fusion protein was secreted to the supernatant of the media and is accumulated. The target protein was expressed over a time of 48 to 120 hours. FIG. 2 shows the electrophoresis result of the time and yield that fusion protein was expressed in the 30 L fermentor. The representative strain of fusion protein of albumin and cell growth factor HSA/hEGF (deposite at China General Microbiological Culture Collection Center: CGMCC No. 2072) expressed a level of fusion protein at different fermentation phases in inorganic high-density media in 30 L fermentor. The fermentation media from different phases were centrifuged and the supernatant is taken to be analyzed with 10% SDS-PAGE. A) standard MW, B) growth phase, C) glycerol fed-batch fermentation, D) methanol induction at 24 hours, E) methanol induction at 48 hours, F) methanol induction at 72 hours. The results indicate the expressed yield of fusion protein (HSA/hEGF) with methanol induction is 0.5-1.2 g/L. When target protein has polymers, the temperature should be increased and methanol induction time should be decreased. The microorganisms and supernatant were separated by Continuous Flow Centrifuge when fermentation was complete.

The embodiments using CHO cells to express fusion protein HSA/hEPO and HSA/hEGF have been described in China Patent ZL02142881.6 China Patent application CN200710057571.9 by Yu, Zailin. Human serum albumin fusion protein used in making skincare products can also be expressed in bacteria, virus, multi-cell animal, transgenic animal and plant.

Embodiment 2

Isolation and Purification of HSA/GF Fusion Protein

The recombinant yeast (ZY-HSA/GF) or mammalian CHO cell express human serum albumin fusion protein HSA/GF and secrete it to the supernatant of the culture media. The media is centrifuged, supernatant is collected and processed by 0.4-1% active charcoal to reduce the salt concentration, and the pH is adjusted to above 7.5. The concentrated sample is filtered through Affi-Gel Blue-gel chromatography column (Bio-Rad). HSA or HSA/GF is bound to the matrix and eluded by a gradient 1-5M NaCl. 75-85% pure protein is obtained. If further purification is necessary, a size exclusion chromatography is applied to make 95-99% or more purity of protein. Pyrogen is removed from the protein samples by use of an Affi-Prep Polymyxin Support (BIO-Rad) column to meet in vivo test requirements. Protein concentration is measured by a standard method such as Bio-Rad Protein Assay Kit. Purified protein is stored in 5% solution of mannitol and PB buffer. The purified protein finally passed through 0.2 µM filter to be sterilized. The method described in the embodiment 8 of China Patent Application CN200710057571.9 by Yu, Zailin and Fu, Yan is used for bio-activity assay on fusion protein and the complex of yeast fermentation supernatant (GX complex is: the concentrated supernatant which contains all the yeast fermentation compounds, such as HSA/GF fusion proteins, fragments of the fusion proteins, yeast proteins, yeast sugar and polysaccharide).

Embodiment 3

Figure 3:
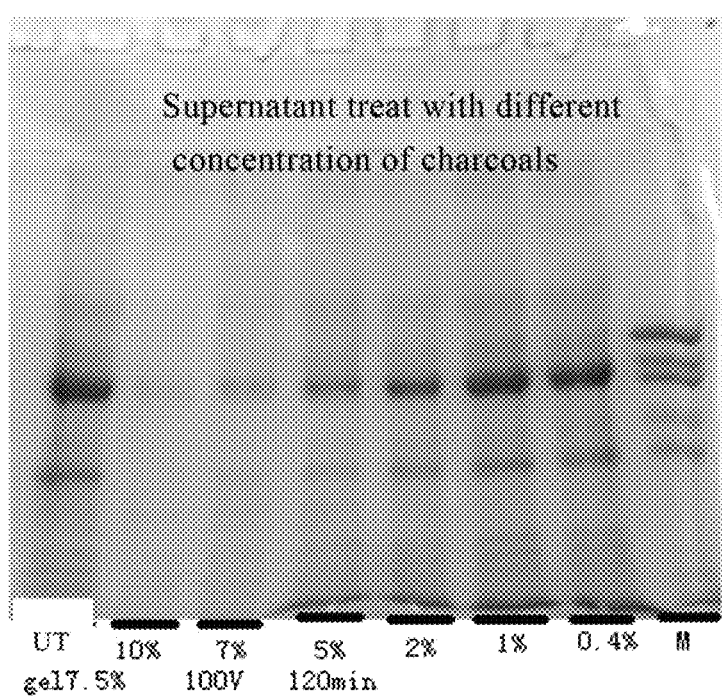
FIGS. 3A-B show SDS-PAGE electrophoresis of the supernatant of fermentation (30 L) comprising fusion protein processed by different concentration of charcoal or diatomite for de-coloring.
Figure 3:
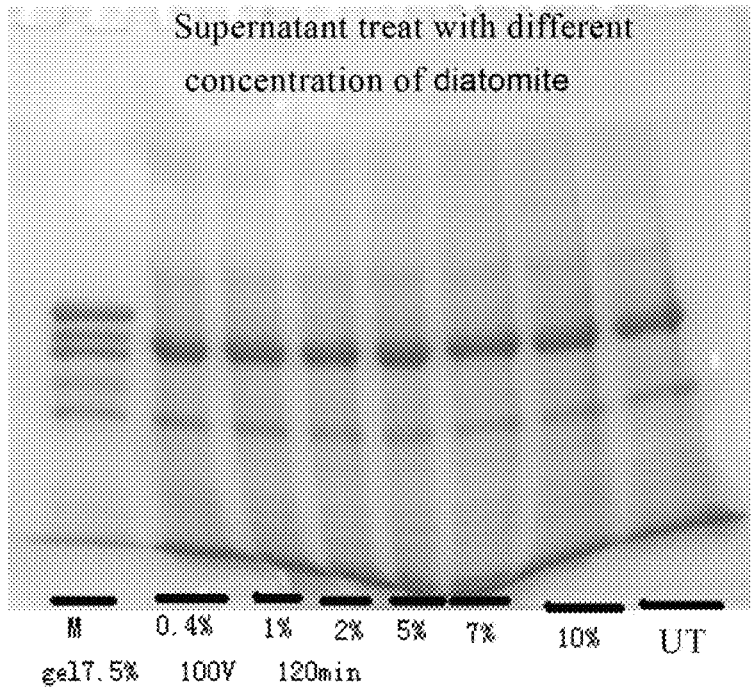
Figure 5:
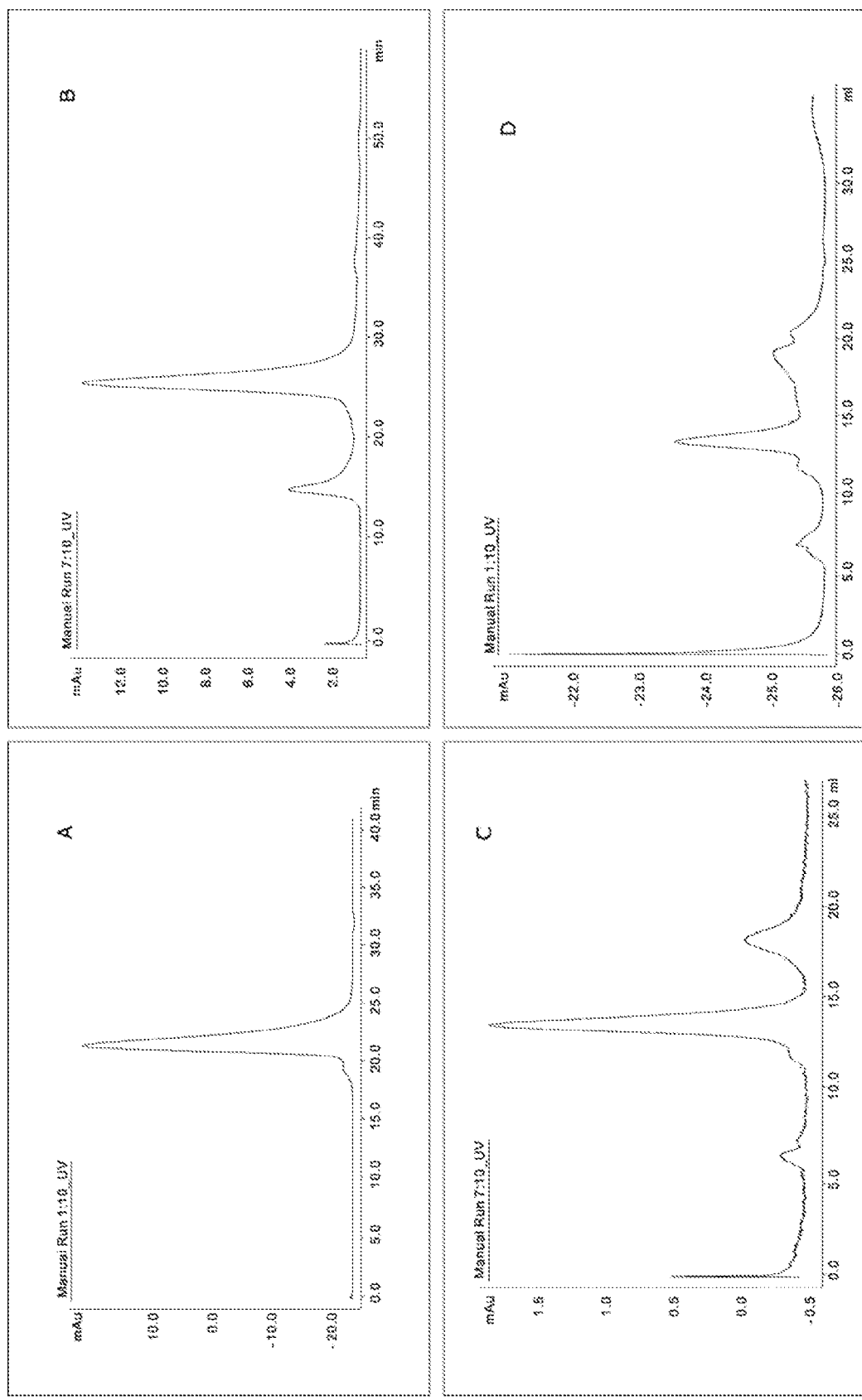
FIG. 5 shows yeast expressed result of fusion protein monomer purity by Superdex 200 column chromatography. A: recombinant HSA/hEGF (72Kd); B: recombinant HSA (65Kd); C: recombinant HSA/hIFN-alpha-2a (87.5Kd); D: recombinant HSA/hGCSF (85Kd).

Preparation of HSA/GF Fusion Protein Active GX Complex Ingredients from Fermentation Media If fermentation supernatant is used for making skincare directly, it is processed preferably by 0.1%-10% active charcoal or diatomite to de-color whose amount is based on A350/280 OD value of yeast pigment; preferably 0.4%, more preferably 2% active charcoal. After being de-colored, the fermentation media is concentrated to 10% of its original volume by a 20K concentration kit, and is further desalted by SEPHADEX G-25 MEDIUM at 30-50% column ratio and transferred to phosphate buffer (PB). The active ingredients (GX complex) of the skincare product is obtained thereof. A large quantity of fusion protein, yeast proteins, fusion protein fragments and yeast polysaccharide compose of active ingredients which improve skin immunization and cell remedy, remove freckles, exfoliate skin and enhance skin elasticity. Total protein of GX complex is assayed by the Bradford method, and total polysaccharide is assayed by the phenol/sulfuric acid method, pigment is assayed by UV/Vis spectroscopy (A350/280). Same results have been obtained from active charcoal-processed fusion proteins or polypeptides from human albumin and various cytokines or cell stimulating factors, or yeast fermentation media. The typical GX complex made has total protein concentration of 20 mg/ml, total polysaccharide 50 mg/ml, UV/Vis spectroscopy ratio 0.075. FIGS. 3A and 3B show SDS-PAGE electrophoresis of fusion protein fermentation media (30L) processed by different concentration of active charcoal or diatomite. 3A) total protein assay on HSA/GCSF fusion protein in 30L fermentation media before and after being processed by different concentration of 0%, 0.4%, 1%, 2%, 5%, 7%, 10% active charcoal. 3B) total protein of fermentation media before processing and after processing with 0%, 0.4%, 1%, 2%, 5%, 7% and 10% diatomite. Same results have been obtained from fusion proteins of human albumin with various cytokines or cell stimulating factors, or polypeptides. Using Diatomite, the supernatant has little loss of total protein, total polysaccharide and pigment as shown by UV absorption data. FIG. 4 shows the results of total protein, total polysaccharide and A350/280 value of fermentation media processed before or after by different concentration of active charcoal (from FIG. 3A). The result indicates active charcoal has good de-coloring effect, whereas Diatomite has not obvious effect on de-coloring. FIG. 5 shows monomer amount of fusion protein in different fermentation media assayed by GE Superdex 200 column chromatography. A: recombinant HSA/hEGF (72Kd); B: recombinant HSA (65Kd); C: recombinant HSA/hIFN-alpha-2 a (87.5Kd); D: recombinant HSA/hGCSF (85Kd).

The bioactivity assay of GX complex ingredient at cell level is similar to the bioactivity assay of purified fusion protein when in same amount of fusion protein.

GX COMPLEX ingredient and purified fusion protein can be added mannitol to 5% concentration, tween 80 to 0.04%, and lyophilized at pH4-7 to store in pharmaceutical ampoules. The product can be applied to the skin after dissolving the lyophilized ingredients in water.

Embodiment 4

Preparation of Aqueous Solution Comprising HSA/GF Fusion Protein for Skincare

The main ingredients of aqueous skincare solution (WN) 1-5% glycerol, 1-8% propanediol, thickener carbomer 1342, 0.5-2% between, 0.1% preservative ethyl p-hydroxybenzoate were mixed with water, then 5-50 mg purified fusion protein were added (cell specific activity 106-8 IU/mg), or alternatively, de-colored, desalted and concentrated 50-500 mg GX complex were added. This was mixed and water added to 100 ml. Filter above solution to remove microorganisms and insoluble materials by 0.45 μm or 0.22 μm filter.

Figure 6:
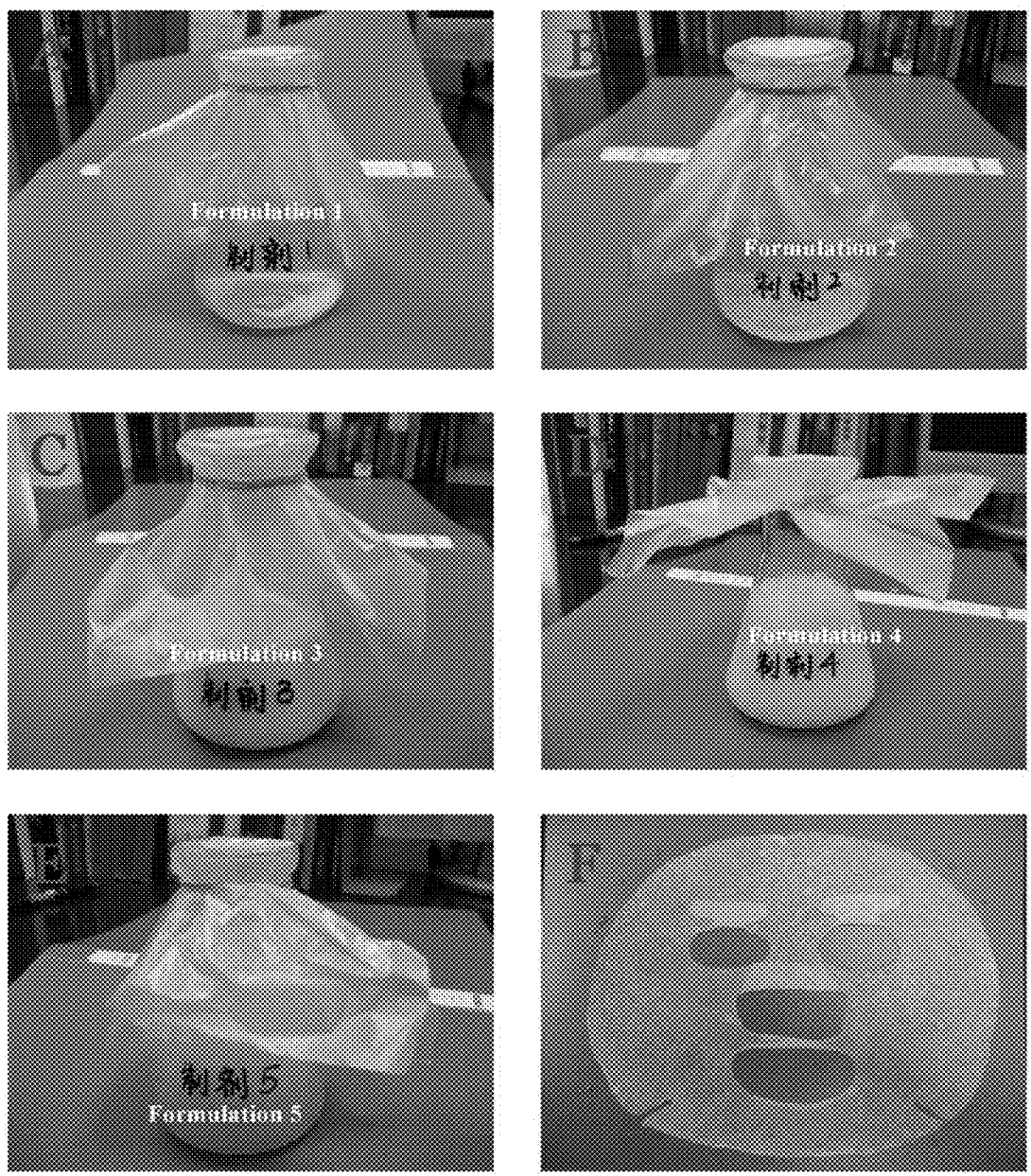
FIGS. 6A-F show six skincare preparations comprising albumin fusion protein.

One embodiment of aqueous solution formulation (preparation 1):

Mix 3 ml glycerol+4 ml propanediol+0.01 ml carbomer 1342+0.1 g ethyl p-hydroxybenzoate+60 ml deionized water until dissolving, add 5-10 mg GX COMPLEX ingredient comprising HSA/hEGF and deionized water to 100 ml. Filter above solution to remove microorganisms and insoluble materials by 0.45 μm filter. This is the aqueous skincare solution comprising fusion protein. (FIG. 6A—preparation 1)

Various human serum albumin fusion proteins with the function of stimulating cell growth and remedy can mix with different concentrations of water retention agents, emulsifiers, thickeners and preservatives or at different ratios to obtain the skincare products disclosed in this embodiment.

This aqueous solution comprising fusion proteins can be used for making spray, shampoo, lotion, softener, fresher and toning water; can be sprayed or applied to face, neck and body; can be applied locally to obtain better topical absorption for whitening and moisturizing skin and to accelerate rejuvenation and reactivation of skin.

For example, it can be made as a transparent or semi-transparent gel when the concentration of the thickener carbomer 1342 is increased from 0.01% to 0.5% Alternatively one can form an oil emulsion, shampoo and lotion. FIG. 6B—preparation-2.

A single fusion protein or GX COMPLEX ingredient can be lyophilized or several fusion proteins or GX COMPLEX ingredients can be mixed with other excipients and lyophilized. The lyophilized product is dissolved in water before use. It has been verified that best lyphilization results when the fusion protein or GX COMPLEX ingredient is lyophilized, mixed with 5% mannitol and phosphate buffer. This formulation can give the fusion protein and GX COMPLEX ingredient longer shelf life at room temperature, and can improve the stability of the active ingredient in skincare products due over long periods of production and marketing.

Embodiment 5

Preparation of an Emulsion Comprising HSA Fusion Protein for Skincare

A skincare emulsion can be Water-in-Oil or Oil-in-Water. For instance, in one embodiment an off-white Preparation 3 can be formulated as follows. Mix 10% glycerol, 2% Tween 80, 3% cholesterol, 5% lecithin, 0.1% ethyl p-hydroxybenzoate and 60 ml water, heat to 45° C. and add fusion protein or GX COMPLEX (same as Embodiment 4), add water to 100 ml and stir at high speed until form emulsion. See FIG. 6C—preparation 3. The above emulsion comprising fusion protein or GX COMPLEX can be used for making face creams, hand creams, shampoos, lotions etc.

Embodiment 6

Preparation of a Cream/Ointment Comprising HSA/GF Fusion Protein for Skincare

An embodiment of an off-white cream/ointment can be formulated as follows. Mix 5% glycerol, 10% Vaseline, 2% lanolin, 1% SLS, 1% Tween 80, 5% polyethylene glycol 400, 2% triglyceride stearic acid, 0.1% preservative ethyl p-hydroxybenzoate and 50% deionized water, heat and stir, and then add fusion protein or GX COMPLEX (same as Embodiment 4) at lower temperature, add deionized water to 100%, stirring continued until a white-color cream/emulsion formed. See FIG. 4D—preparation 4. This preparation can be used for making face creams, eye creams, Sun-screens, cold cream, face ointments, eye ointments, lip ointments, tooth paste. Kojic acid, arbutin, Vitamin C and/or Vitamin E can be added for whitening product.

Embodiment 7

Combination of HSA/GF Fusion Protein and Antibiotics and its Effect for Skincare Acne treatment skincare products (FIG. 6E—preparation 5) can be made by adding 0.2% antibiotics such as Sulfasalazine to the preparation of embodiment 6. Applying this preparation topically relieves local infection. Other antibiotics such as gentamicin, neomycin, oxytetracycline, mupirocin, amidacin, fusidic acid, aureomycin, tetracycline, metronidazole can be used to make a functional skincare product for treating acne and its lesions. Combined formulations with interferon can be used for treating virus infection. Formulation with anti-fungal or anti-allergy medicines can be used for treating infection or inhibit dermatitis.

Embodiment 8

Preparation of Membranes Comprising HSA/GF Fusion Protein for Skincare

Shaped face membrane can be prepared by soaking commercial face membrane in aqueous solution prepared from embodiment 4 (FIG. 4: F-face membrane). Other carrier materials like cotton, non-woven fabrics, gauze, wood pulp, bio-fibre etc. can be used for making face membrane, neck membrane, nose membrane, eye membrane and body membrane. Water is added and stirred to form a peelable mask membrane, paste mask membrane, powder mask membrane, and mixed mask membranes. Therefore, commercial masks membrane can be combined with an aqueous solution preparation comprising fusion protein or yeast protein and polysaccharide (to decrease added water volume).

Embodiment 9

The Effect of the Skincare Product Containing of HSA/GF Fusion Protein

Eighteen volunteers, age 24-55, were divided randomly to three-person groups and used aqueous solution preparation, face membrane, face cream, body lotion (emulsion), eye cream and acne-off cream. Under double-blind conditions, each person from each group used basic vehicle formulation; another person used basic vehicle formulation with purified HSA/hEGF fusion protein; the last person used basic vehicle formulation with GX COMPLEX. All subjects were informed that the product applied to their skin might be the one comprising fusion protein or not comprising fusion protein. Ten days later, self-evaluations were obtained, and treatment continued another ten-days. The result indicated the 10 day-trial meet anticipation 67% (12 of 18 people positive), 20 day-trial meet anticipation around 83% (15 of 18 people positive), 30 day-trial meet anticipation around 100% (18 of 18 people positive). Proper applying procedure should be considered in order to obtain good effect from fusion protein skincare. For instance, complete face cleaning should be done before using aqueous solution preparation comprising fusion protein, and let skincare to stay at least ten minutes to be absorbed after smoothing over, and then smooth over skincare comprising or not comprising fusion protein, Sunscreen, toning. The skincare products comprising HSA/GF fusion protein has the best biological effect.

Embodiment 10

Preparation of Combined HAS/GF Fusion Protein for Skincare Products

Skincare comprising combined HSA/GF fusion proteins having more than one kind of human fusion albumin protein. For instance, mix HSA/hEGF, HSA/bFGF and HSA/KGF-2 with minimum 80% purity at same proportion, or mix GX Complex from fementation media according to the proportion of total protein and polysaccharide and add to aqueous solution preparation from embodiment 4. The result from volunteers' trial indicated the skincare with these formulations have better effect on smoothing skin than the skincare with fusion protein monomer (20 days-trial meet anticipation 90%).

Embodiment 11

Assay on Stability of Skincare Product Comprising HSA Fusion Protein

For the examples of HSA/bFGF, HSA/hEGF and HSA/KGF-2, the stability of HSA/GF was assayed at different time period and at room temperature or/and at 40° C. incubator. The formulation of an aqueous preparation is same as that of embodiment 4. The control is the aqueous preparation comprising 10000 IU (International Unit) of rEGF, produced by bacterial or just the aqueous preparation. Aqueous preparation with 10000 IU HSA/hEGF (serial 2) or 10000 IU purified HSA/hKGF-2 (serial 3) or 10000 IU HSA/bFGF or two kind of fusion proteins of HSA/hEGF (5000 IU) and HSA/bFGF (5000 IU) combination or three kind of fusion proteins combination of HSA/EGF, HSA/KGF-2, HSA/bFGF (3300 IU of each). Aqueous preparation with GX COMPLEX are stored in tubes at room temperature or 37° C. incubator. 200 μl of above combination samples each was collected every 7-dys, and put in −80° C. freezer. After all the samples had been collected, they were tested for the bio-activity on BalBC3T3 cell bioassay. The control sample was tested on the same time. The result indicated:

A. the HSA/GF fusion protein has a much longer half-life than cytokine monomer (alone) at all storage (during the therapeutic treating) conditions, compared the fusion protein molecule of GF with HSA. GF monomer's half-life is one week at 37° C., or 2 weeks at room temperature in aqueous solution; fusion protein's half-life is 12 weeks at 37° C. or 24 weeks at room temperature in aqueous solution (12 times longer half life). The purified HSA/GF keeps its activity after 24 weeks at room temperature in the same aqueous solution, and keeps most activity at 37° C. after 12 weeks. Whereas, rEGF monomer loses its activity at room temperature in same aqueous solution after 2 weeks.

B. Fusion protein monomer in GX COMPLEX form, the fusion protein has a half-life that is twice as long as that of the purified fusion protein monomer in same aqueous solution.

C. The test result also indicated skincare formulation (aqueous preparation) has a better protective effect to various protein ingredients such as GF monomer, fusion protein monomer or GX Complex than only in regular phosphate buffer.

D. The bioactivity has no difference during storage (shelf-life) for combined fusion proteins and fusion protein monomer at same mole of various preparations and buffers.

Cell growth factor (GF) has extended shelf life after fusing with serum albumin. This characteristic facilitates better biostability and environmental resistance for skincare.

It can be anticipated that other forms of skincare such as emulsion, cream and paste should have similar protection for HSA/GF fusion protein.

Although the preferable embodiments have been described in the present invention, the common technology persons would understand that they can modify formats and details in various ways under the premise of non-deviating from claims of present invention.

What is claimed is:

1. A method of skincare comprising topically applying a skincare composition to a subject, said skincare composition comprising a non-glycosylated human serum albumin (HSA)/human epidermal cell growth factor (hEGF) fusion protein expressed in *Pichia pastoris*, wherein the *Pichia pastoris* used in expression of the non-glycosylated HSA/hEGF fusion protein is a yeast expression strain in Deposit No. CGMCC 2072 at China General Microbiological Culture Collection (CGMCC) center.

2. The method of claim 1, wherein the skincare composition is applied to the subject daily.

3. The method of claim 1, wherein the skincare composition is applied to the subject in a form of cream, lotion, emulsion, aqueous solution, ointment, suppository, freshness toning water, shampoo, conditioner, deodorant liquid, gargle, or tooth paste.

4. The method of claim 1, wherein the skincare composition is applied to the subject in a form of face membrane, neck membrane, nose membrane, eye membrane, or body membrane.

5. The method of claim 1, wherein said topically applying the skincare composition stimulates rejuvenation and reactivation of skin cells, and achieves moisture retention, wrinkle removal or prevention, freckle removal, or skin whitening.

6. The method of claim 1, wherein said topically applying the skincare composition treats ulcerations, wounds, or burns of the subject.

7. The method of claim 1 further comprising topically applying said skincare composition that further comprises another fusion protein selected from the group consisting of HSA/keratinocyte growth factor (KGF), HSA/insulin-like growth factor (IGF), HSA/platelet-derived growth factor (PDGF), and combinations of any thereof.

8. The method of claim 1 further comprising topically applying said skincare composition that further comprises an additive selected from the group consisting of HSA, HSA/granulocyte colony stimulating factor (GCSF), HSA/interferon (IFN), HSA/interleukin (IL), and combinations of any thereof.

9. The method of claim 1 further comprising topically applying said skincare composition that further comprises a concentrated supernatant of a yeast culture media containing yeast fermentation compounds comprising yeast sugar and polysaccharide, yeast proteins and the fusion protein and fragments thereof expressed therein.

10. A method of producing a skincare composition comprising a non-glycosylated human serum albumin (HSA)/human epidermal cell growth factor (hEGF) fusion protein expressed in *Pichia pastoris*, wherein the *Pichia pastoris* used in expression of the non-glycosylated HSA/hEGF fusion protein is a yeast expression strain in Deposit No. CGMCC 2072 at China General Microbiological Culture Collection (CGMCC) center, said method comprising:
   i) expressing the fusion protein using said yeast expression strain;
   ii) purifying the fusion protein obtained in i); and
   iii) adding the fusion protein purified from ii) to the skincare composition.

11. The method of claim 10, wherein the fusion protein is purified by column chromatography.

12. A method of producing a skincare composition comprising a non-glycosylated human serum albumin (HSA)/human epidermal cell growth factor (hEGF) fusion protein expressed in *Pichia pastoris*, wherein the *Pichia pastoris* used in expression of the non-glycosylated HSA/hEGF fusion protein is a yeast expression strain in Deposit No. CGMCC 2072 at China General Microbiological Culture Collection (CGMCC) center, said method comprising:
   i) expressing the fusion protein using said yeast expression strain in a yeast culture medium;
   ii) centrifuging the yeast culture medium obtained from i);
   iii) de-coloring a supernatant obtained from ii);
   iv) de-salting the supernatant obtained from iii);
   v) concentrating the supernatant obtained from iv); and
   vi) adding a product from v) to the skincare composition.

13. The method of claim 12 further comprising mixing fermentation media which express at least two types of fusion proteins before step ii).

14. The method of claim 12 further comprising lyophilizing the product from step v).

15. The method of claim 12, wherein in iii) said de-coloring the supernatant uses 0.1%-10% (w/w) active charcoal, or diatomite.

\* \* \* \* \*